(12) United States Patent
Nakamae et al.

(10) Patent No.: US 12,153,008 B2
(45) Date of Patent: Nov. 26, 2024

(54) SENSOR UNIT AND CELL CULTURE ANALYSIS DEVICE COMPRISING SAME

(71) Applicant: PHC Holdings Corporation, Tokyo (JP)

(72) Inventors: Kenta Nakamae, Ehime (JP); Masahiro Kouge, Ehime (JP); Shingo Otani, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 489 days.

(21) Appl. No.: 17/620,257

(22) PCT Filed: Oct. 20, 2020

(86) PCT No.: PCT/JP2020/039463
§ 371 (c)(1),
(2) Date: Dec. 17, 2021

(87) PCT Pub. No.: WO2021/079892
PCT Pub. Date: Apr. 29, 2021

(65) Prior Publication Data
US 2022/0365020 A1 Nov. 17, 2022

(30) Foreign Application Priority Data
Oct. 21, 2019 (JP) .................... 2019-191855

(51) Int. Cl.
*G01N 27/28* (2006.01)
*C12M 1/34* (2006.01)

(52) U.S. Cl.
CPC .......... *G01N 27/283* (2013.01); *C12M 41/30* (2013.01)

(58) Field of Classification Search
CPC ............. G01N 27/283; G01N 33/4835; G01N 33/48735; C12M 41/30
See application file for complete search history.

(56) References Cited

U.S. PATENT DOCUMENTS 5,568,806 A * 10/1996 Cheney, II ............ A61B 5/6849
600/373
8,974,386 B2 * 3/2015 Peyser ............... A61B 5/14546
600/365

(Continued)

FOREIGN PATENT DOCUMENTS

EP 2 636 372 9/2013
GB 2 049 199 12/1980

(Continued)

OTHER PUBLICATIONS

EPO machine-generated English language translation of JP 2008-26178 A, patented Feb. 7, 2008 (Year: 2008).*

(Continued)

*Primary Examiner* — Alexander S Noguerola
(74) *Attorney, Agent, or Firm* — Wenderoth, Lind & Ponack, L.L.P.

(57) ABSTRACT

A sensor unit (9) comprises a substrate (13) having a sensor (16), wiring (19) connected to the sensor (16), connection portions (20a, 20b) connected to the sensor (16) via the wiring (19), and a bent portion (17) where the sensor (16) is bent downward. The sensor (16) is formed so as to be cut out from the substrate (13) in a state in which the bent portion (17) remains on the substrate (13).

16 Claims, 28 Drawing Sheets

(56) References Cited

U.S. PATENT DOCUMENTS

| | | |
|---|---|---|
| 9,170,255 B2 | 10/2015 | Teich et al. |
| 2007/0000776 A1 | 1/2007 | Karube et al. |
| 2009/0048499 A1 | 2/2009 | Glejbol |
| 2009/0071830 A1* | 3/2009 | Vann ................ G01N 27/44782 |
| | | 204/627 |
| 2010/0263462 A1 | 10/2010 | Nakamura |

FOREIGN PATENT DOCUMENTS

| | | |
|---|---|---|
| JP | 10-276762 | 10/1998 |
| JP | 2002-361028 | 12/2002 |
| JP | 2004-112092 | 4/2004 |
| JP | 2005-233917 | 9/2005 |
| JP | 2008-26178 | 2/2008 |
| JP | 2008-516714 | 5/2008 |
| JP | 2010-272857 | 12/2010 |
| WO | 2008/008149 | 1/2008 |
| WO | 2015/109192 | 7/2015 |

OTHER PUBLICATIONS

EPO machine-generated English language translation of JP 10-276762 A, patented Oct. 20, 1998 (Year: 1998).*

EPO machine-generated English language translation of JP 2002-361028 A, patented Dec. 17, 2002 (Year: 2002).*

Extended European Search Report issued Nov. 21, 2022 in European Patent Application No. 20879728.2.

International Search Report issued Dec. 28, 2020 in International (PCT) Application No. PCT/JP2020/039463.

* cited by examiner

SENSOR UNIT AND CELL CULTURE ANALYSIS DEVICE COMPRISING SAME

TECHNICAL FIELD

The present invention relates to a sensor unit used for analysis of a cell culture, and to a cell culture analysis device comprising this sensor unit.

BACKGROUND ART

A conventional cell culture analysis device is configured such that a sensor is fixed to a through-hole portion provided to a substrate, and a lead wire for taking off signals is connected to this sensor.

More specifically, a sensor for monitoring the state of a culture medium is inserted into a cell culture vessel, and an electrical connection terminal is provided to the sensor. The lead wiring connected to the connection terminal is connected to an external control unit (for example, Patent Literature 1).

Also disclosed is a cell culture analysis device having a cartridge that mates with a plate provided with a plurality of cell culture vessels. This analysis device has sensors that measure the inside of each culture vessel, and the cartridge is provided with a plurality of openings into which these sensors are inserted. The sensors and fiber cables are connected within the openings. These fiber cables are connected to an external control unit (for example, Patent Literature 2).

CITATION LIST

Patent Literature

Patent Literature 1: JP-A 2004-112092
Patent Literature 2: U.S. Pat. No. 9,170,255

SUMMARY

Technical Problem

In the above-mentioned prior art, the sensor is immersed in a medium in a culture medium, for example, and senses the environment in the medium.

With a cell culture device, a plurality of culture vessels are usually disposed for analysis of cell culture, which means that a large number of sensors are needed for these vessels, so the cell culture analysis device needs to be made more compact.

In view of this, it is an object of the present invention to reduce the size of a cell culture analysis device.

Solution to Problem

To achieve this object, the sensor unit of the present invention comprises a substrate having a sensor, wiring that is connected to the sensor, connection portions that are connected to the sensor via the wiring, and a bent portion where the sensor is bent downward. The sensor is formed by being cut out from the substrate, leaving the bent portion on the substrate.

Technical Effects

With the sensor unit of the present invention, the sensor is formed by being cut out from the substrate, leaving behind the bent portion where the sensor is bent downward on the substrate, and therefore no component is needed for fixing the sensor to the substrate, so the sensor unit can be more compact.

DESCRIPTION OF EMBODIMENTS

The sensor unit 9 according to an embodiment of the present invention and a cell culture analysis device 3 comprising the sensor unit 9 will now be described with reference to the appended drawings.

Overview of Cell Culture Device

Figure 1:
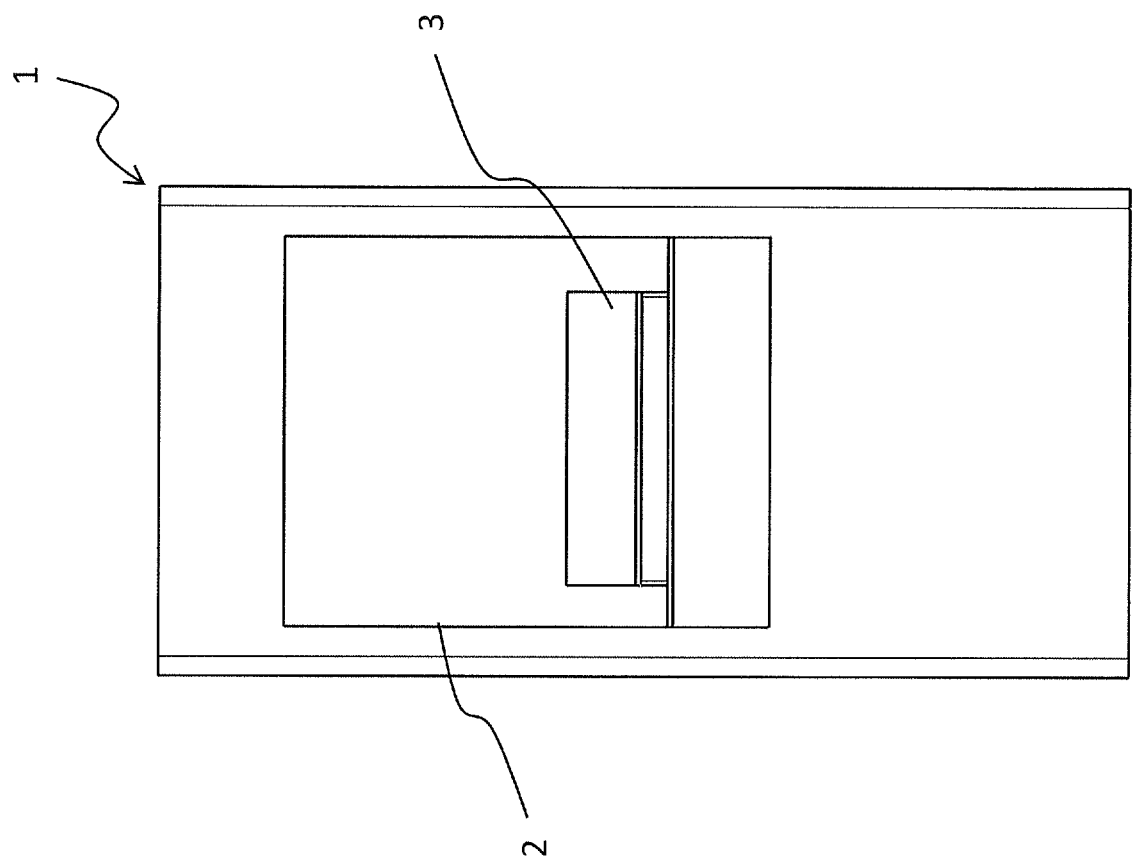
FIG. 1 is a front view of a cell culture device equipped with a cell culture analysis device comprising the sensor unit according to an embodiment of the present invention.
Figure 2:
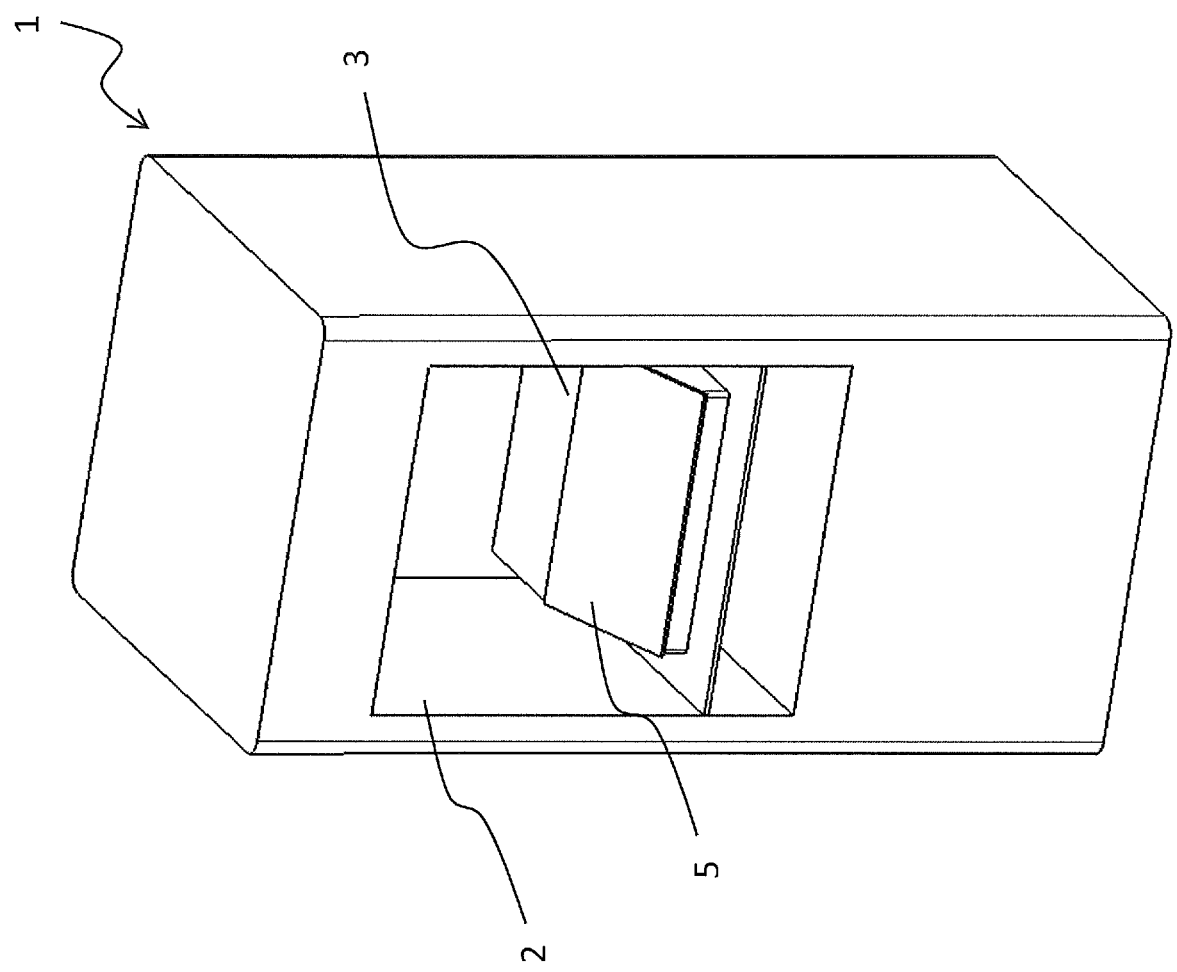
FIG. 2 is an oblique view of the cell culture device of FIG. 1.
Figure 3:
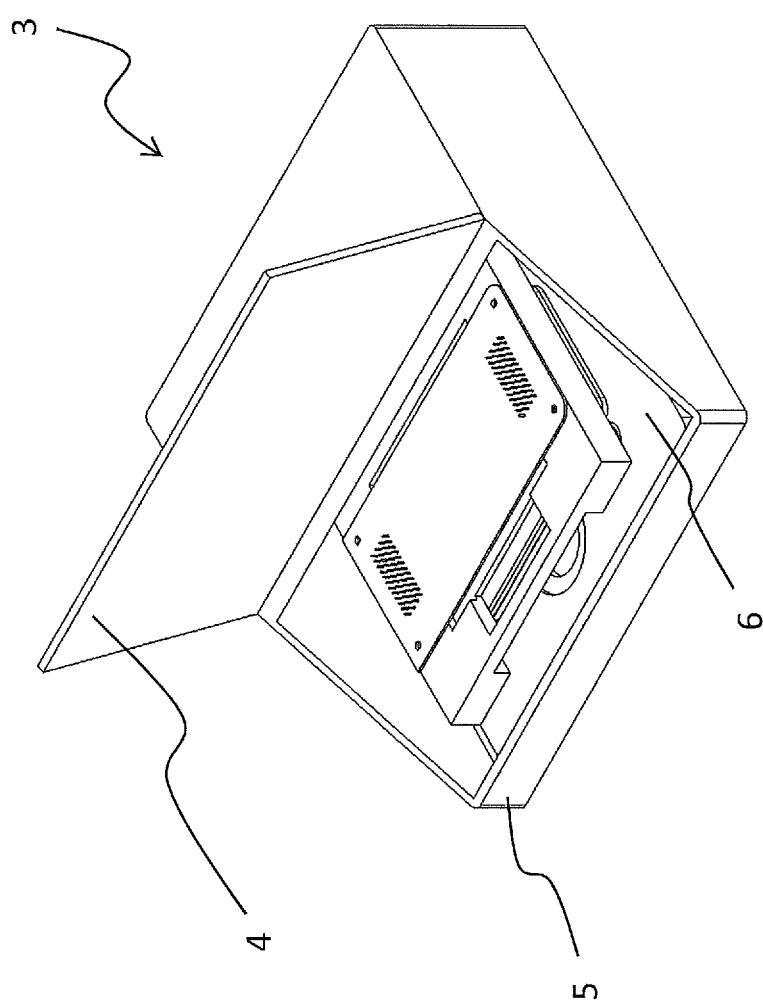
FIG. 3 is an oblique view of the cell culture analysis device of FIG. 1.

FIGS. 1 and 2 show a cell culture device 1, in which the cell culture analysis device 3 is disposed inside a culture chamber 2. Although not shown in FIGS. 1 and 2, a door that can be opened and closed is disposed on the front surface of the culture chamber 2. That is, in the culture chamber 2, cell culture is performed using the cell culture analysis device 3 shown in FIG. 3, and the culture status is sensed.

Figure 4:
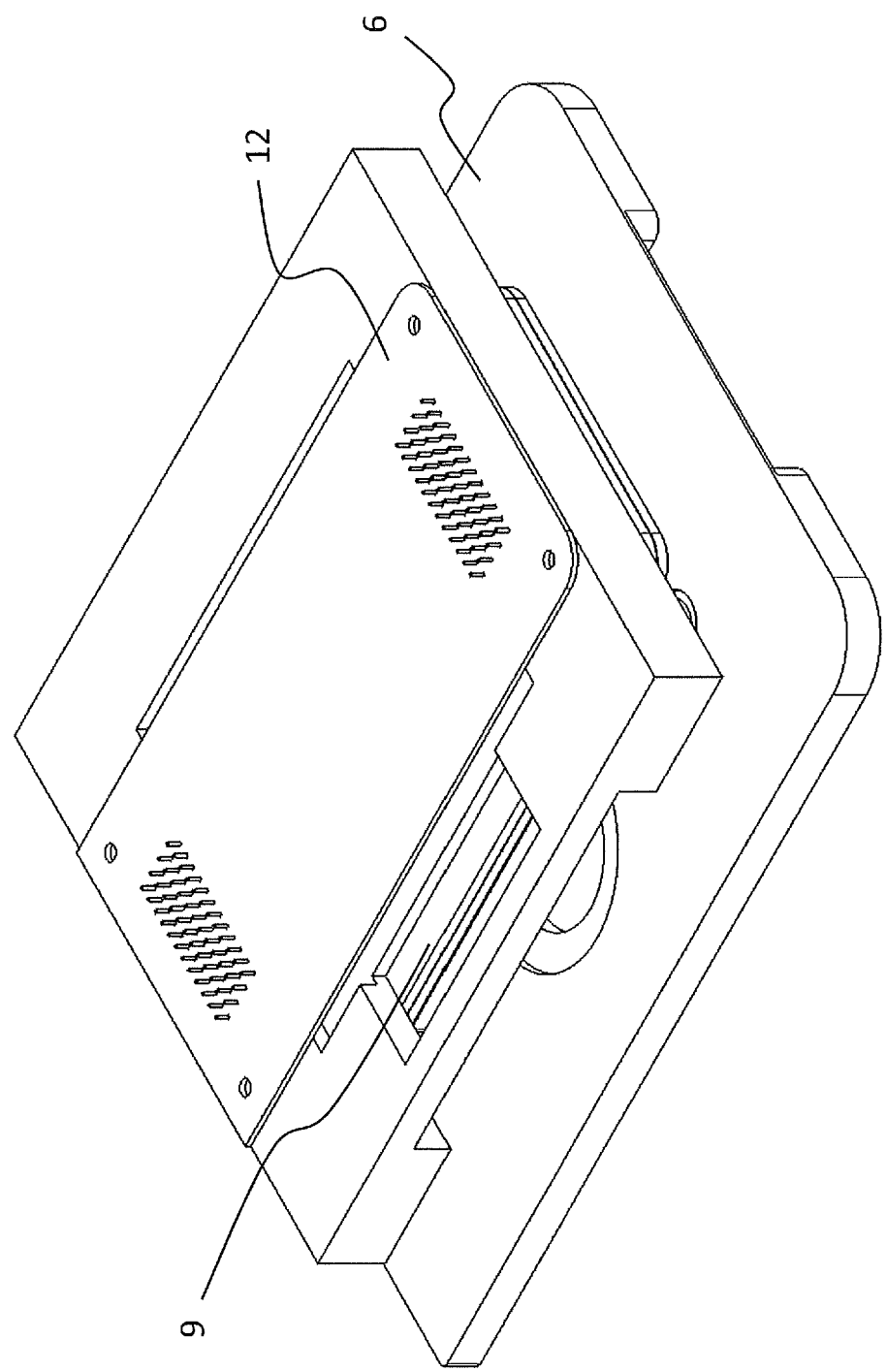
FIG. 4 is an oblique view of the cell culture analysis device of FIG. 1.
Figure 5:
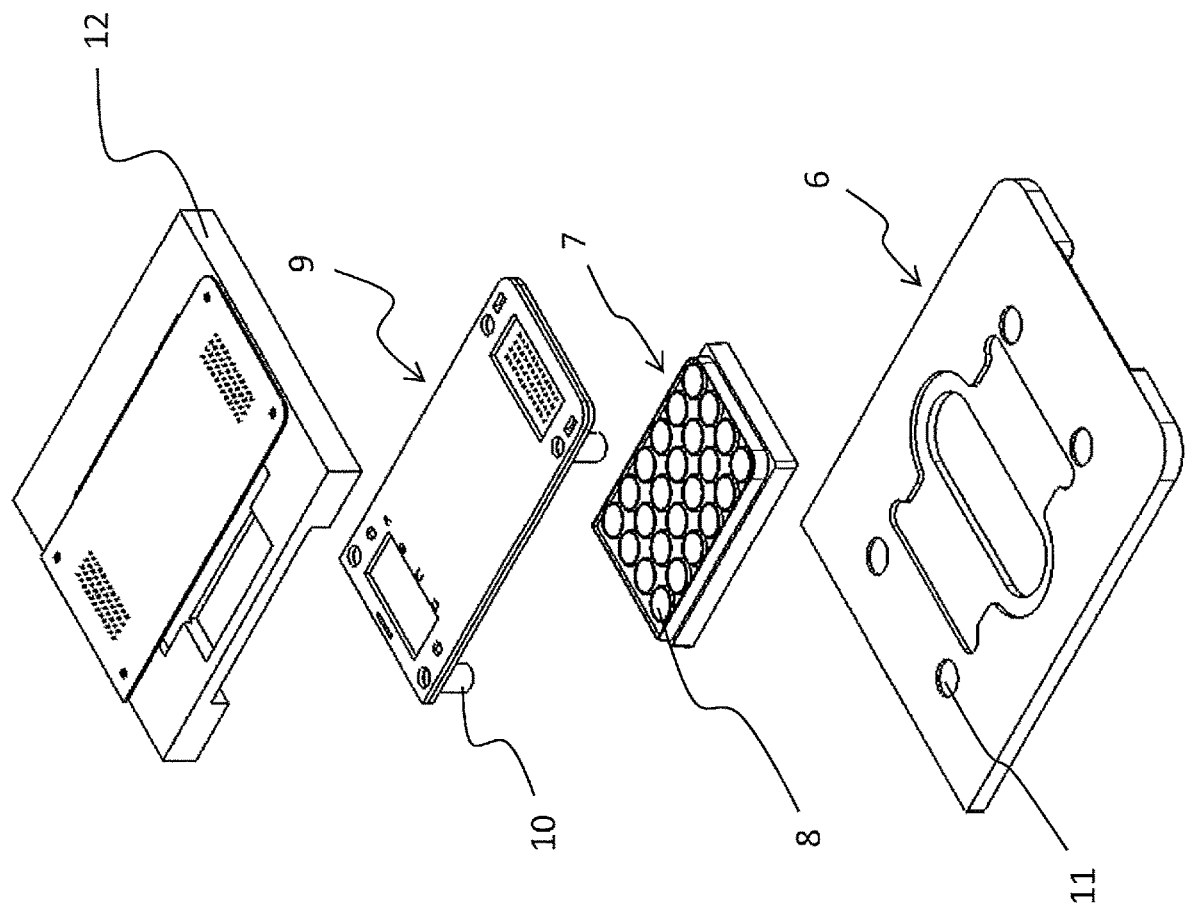
FIG. 5 is an exploded oblique view of the cell culture analysis device of FIG. 1.
Figure 6:
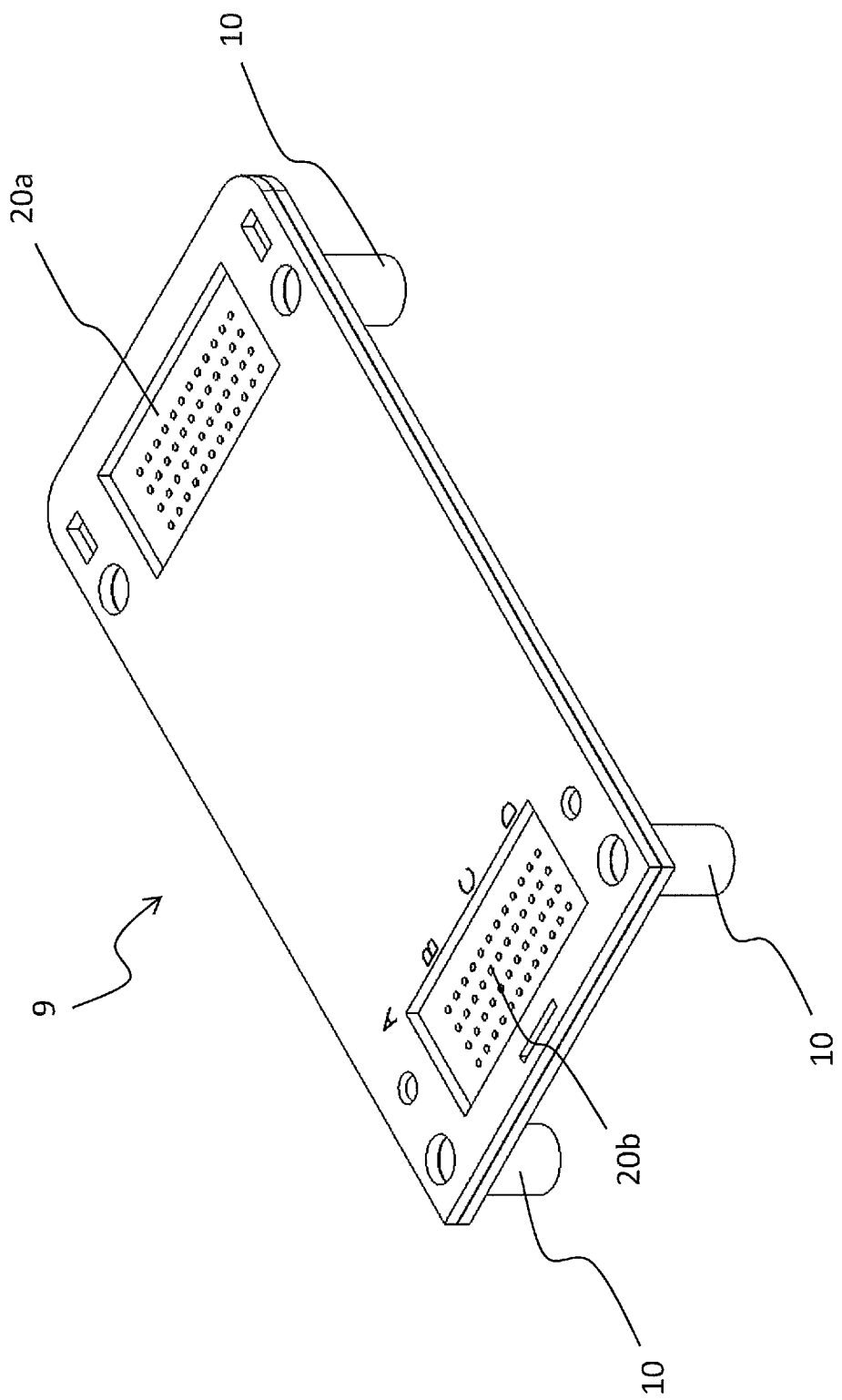
FIG. 6 is a detail oblique view of the sensor unit of FIG. 1.

As shown in FIGS. 4 to 6, in the cell culture analysis device 3, a culture vessel installation part 6 is disposed inside a main body case 5 provided with a door 4 on the front side. A culture vessel 7 is placed on the culture vessel installation part 6. The culture vessel 7 is equipped with 24 wells 8, for example.

In this state, the sensor unit 9 is disposed on the culture vessel 7. The sensor unit 9 has four legs (support portions) 10 provided on the lower surface side thereof, and these legs are inserted into positioning holes 11 provided to the culture vessel installation part 6 so that the sensor unit 9 is disposed a specific distance away above the culture vessel 7. That is, the sensor unit 9 is provided with the legs (support portions) 10 for ensuring housing spaces for the wells 8 (culture vessels) on the culture vessel installation part 6. The sensor unit 9 is supported on the culture vessel installation part 6 by the legs (support portions) 10.

As described above, the legs (support portions) 10 support the sensor unit 9 with respect to the culture vessel installation part 6 in order to ensure housing spaces for the wells 8 (culture vessels) on the culture vessel installation part 6. Here, the support portions that support the sensor unit 9 are not limited to being legs provided to the sensor unit 9. For instance, these may be support bodies that support the sensor unit 9 from below with respect to the culture vessel installation part 6.

A control unit 12 is also disposed on the sensor unit 9.

The control unit 12 controls the sensor unit 9 by applying voltage to the sensor unit 9 via connection portions 20a and 20b. The control unit 12 then transmits the culture status to a data processing device (such as a personal computer) outside of the cell culture device 1.

Figure 7:
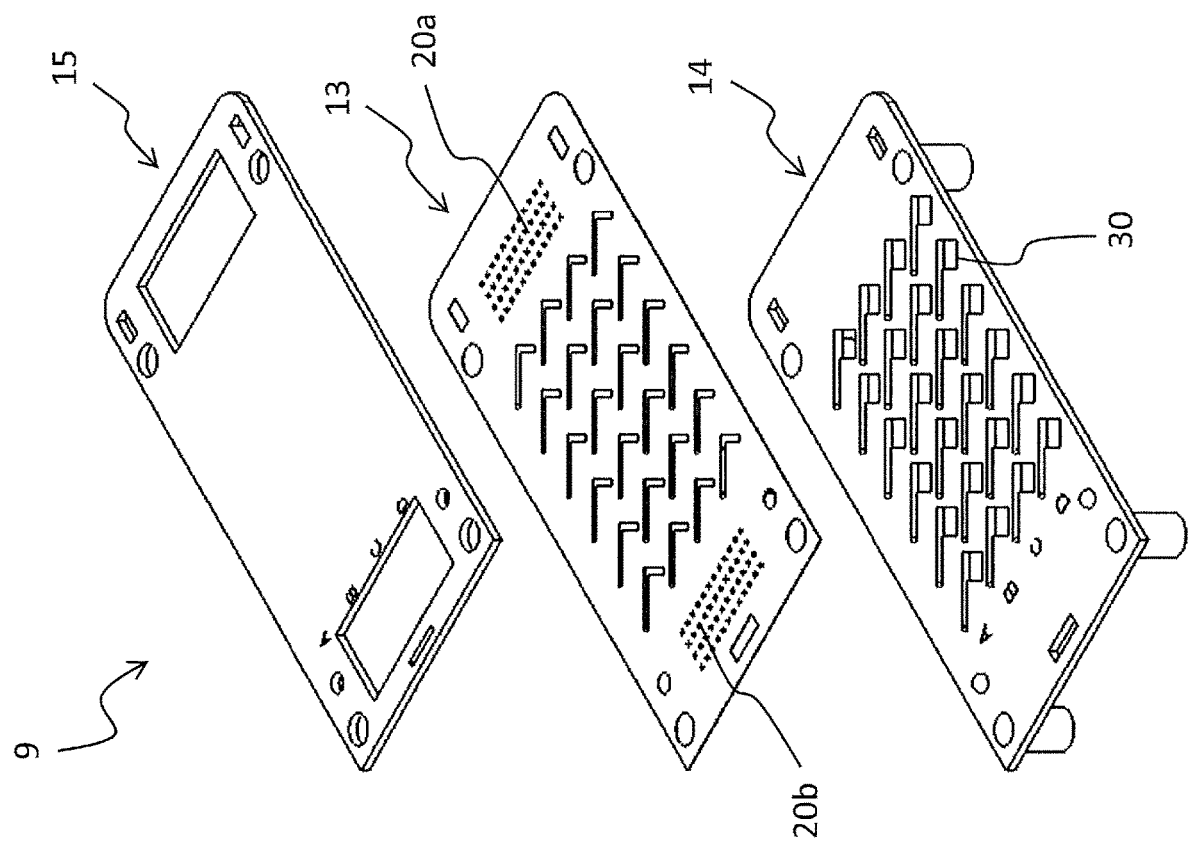
FIG. 7 is an exploded oblique view of the sensor unit of FIG. 1.
Figure 8:
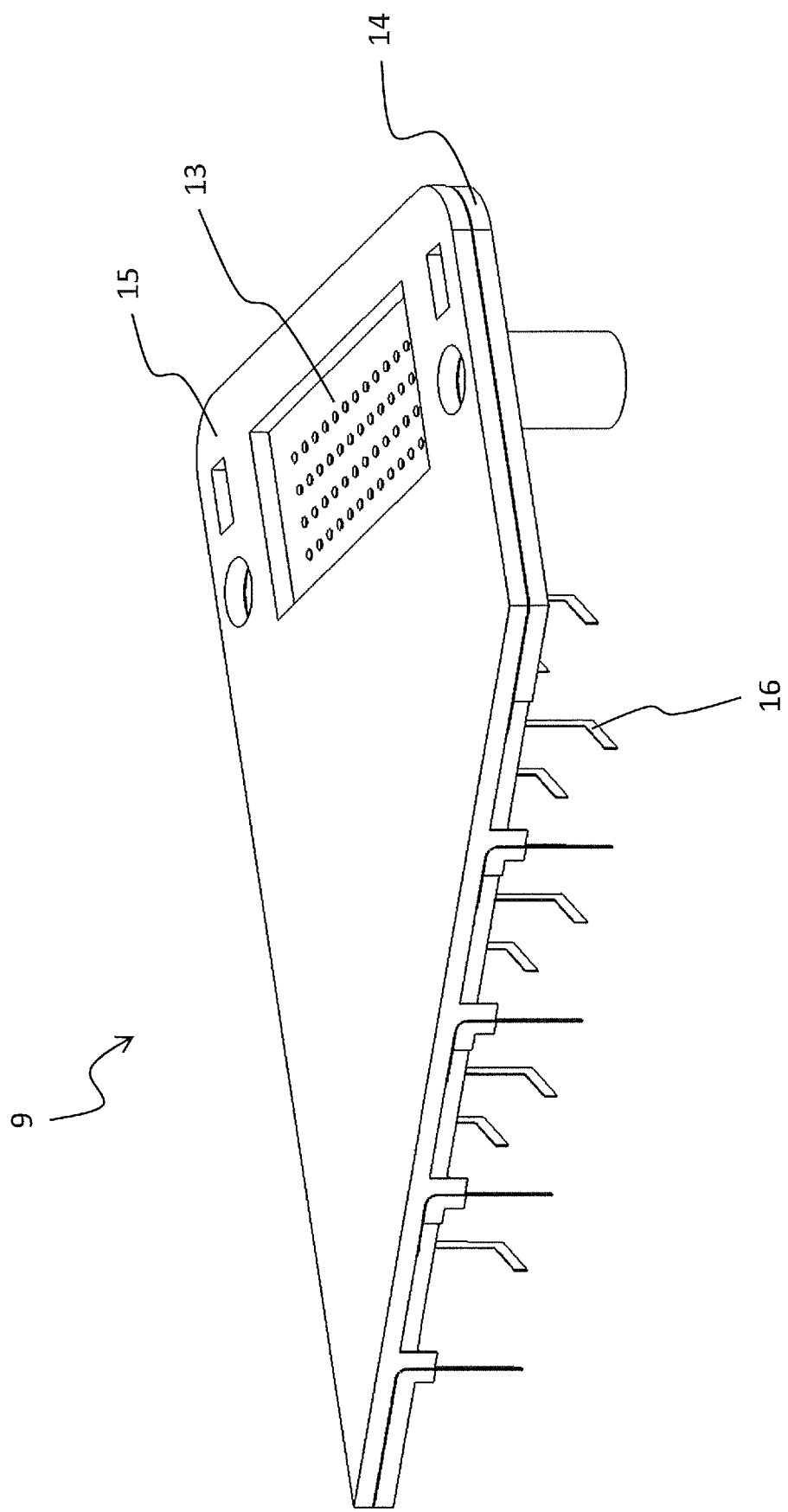
FIG. 8 is a partially cut-away oblique view of the sensor unit of FIG. 1.

As shown in FIGS. 6 to 8, the sensor unit 9 comprises a substrate 13 made of PET (polyethylene terephthalate), which is a resin material, a bottom cover 14 that is disposed below the substrate 13, and a top cover 15 that is disposed above the substrate 13. The substrate 13 is sandwiched from above and below by the bottom cover 14 and the top cover 15.

As shown in FIGS. 8 to 11, the substrate 13 is provided with a plurality of sensors 16. More specifically, the sensors 16 are formed so as to be cut out from the substrate 13, leaving on the substrate 13 a bent portion 17 where the connection portion between the sensor 16 and the substrate 13 is bent downward.

As shown in FIG. 8, the sensor 16 of the present embodiment is substantially L-shaped.

Figure 9:
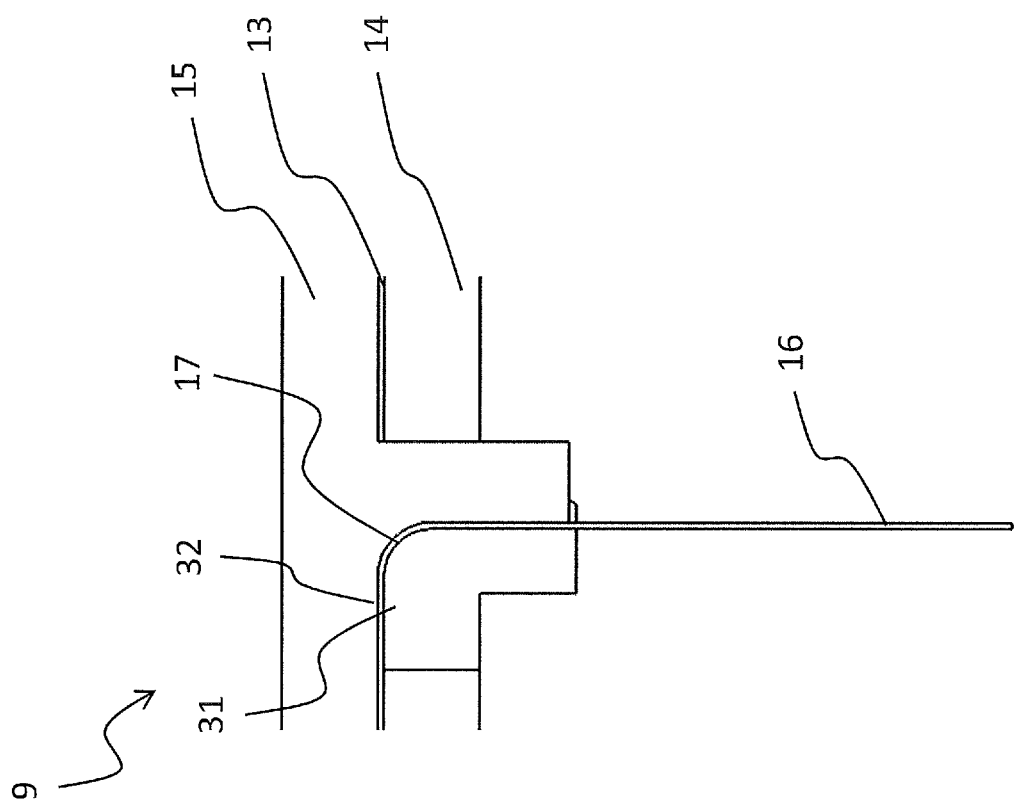
FIG. 9 is a partially detail cross-sectional view of the sensor unit of FIG. 1.

FIG. 9 shows a detail cross-sectional view of FIG. 8. With the sensor 16 in this embodiment, as shown in FIG. 9, the upper portion of the substantially L-shaped vertical side is a bent portion 17.

Figure 10:
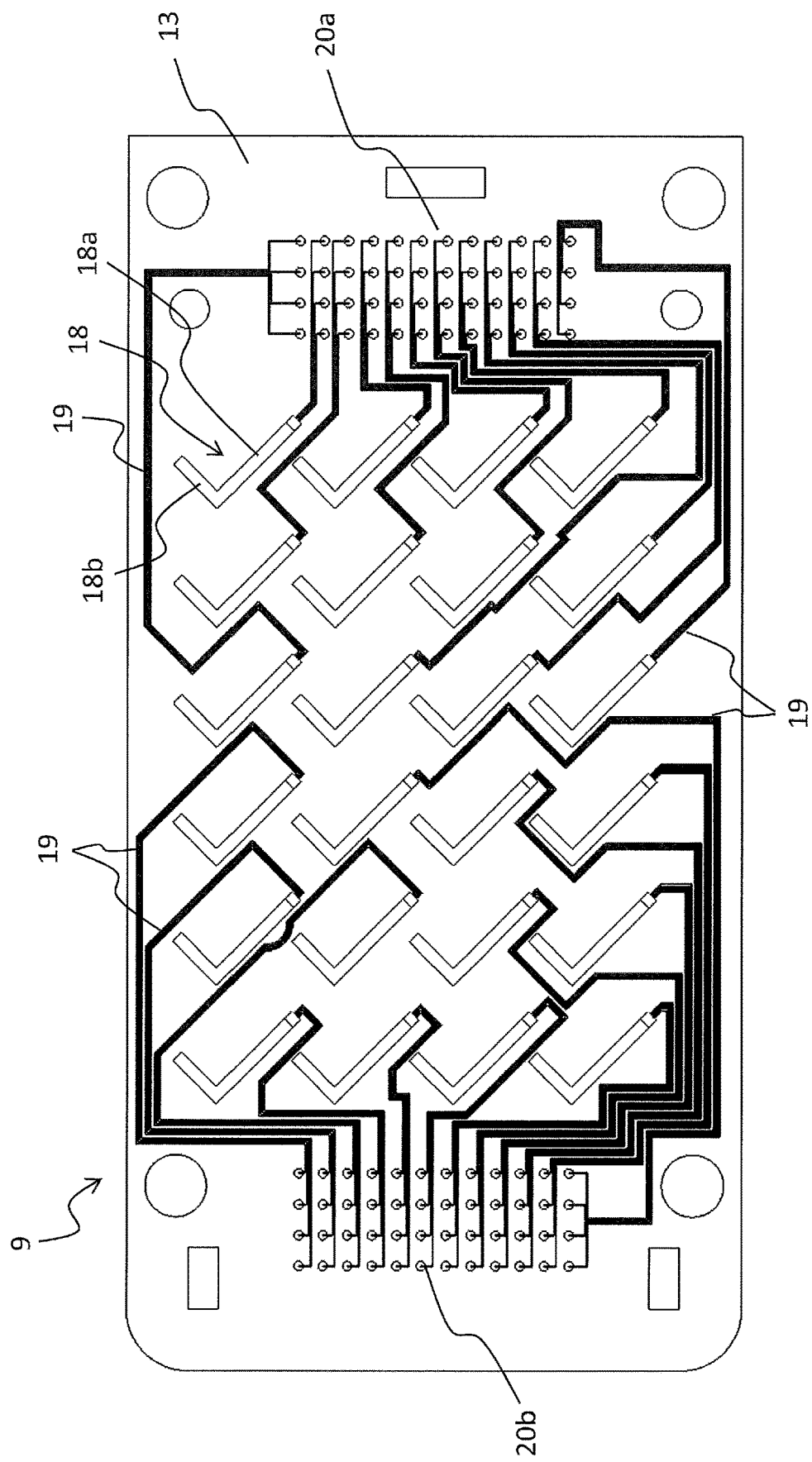
FIG. 10 is a partial plan view of the sensor unit of FIG. 1.

The substantially L-shaped portions 18 of the substrate 13 shown in FIG. 10 are openings made by cutting out the substantially L-shaped sensors 16. More specifically, the substrate 13 has a rectangular shape, and the vertical side of the substantially L-shaped sensor 16 is cut out from the substrate 13 in a state of being inclined with respect to the two opposing sides of the substrate 13.

Also, as shown in FIG. 10, wiring 19 on the substrate 13 connected to the bent portion 17 of the sensor 16 is pulled out to the outer peripheral portion of the substrate 13 in between a vertical side cutout portion 18a of adjacent sensors 16 (first sensor) and a lateral side cutout portion 18b of the sensor 16 (second sensor).

Figure 11:
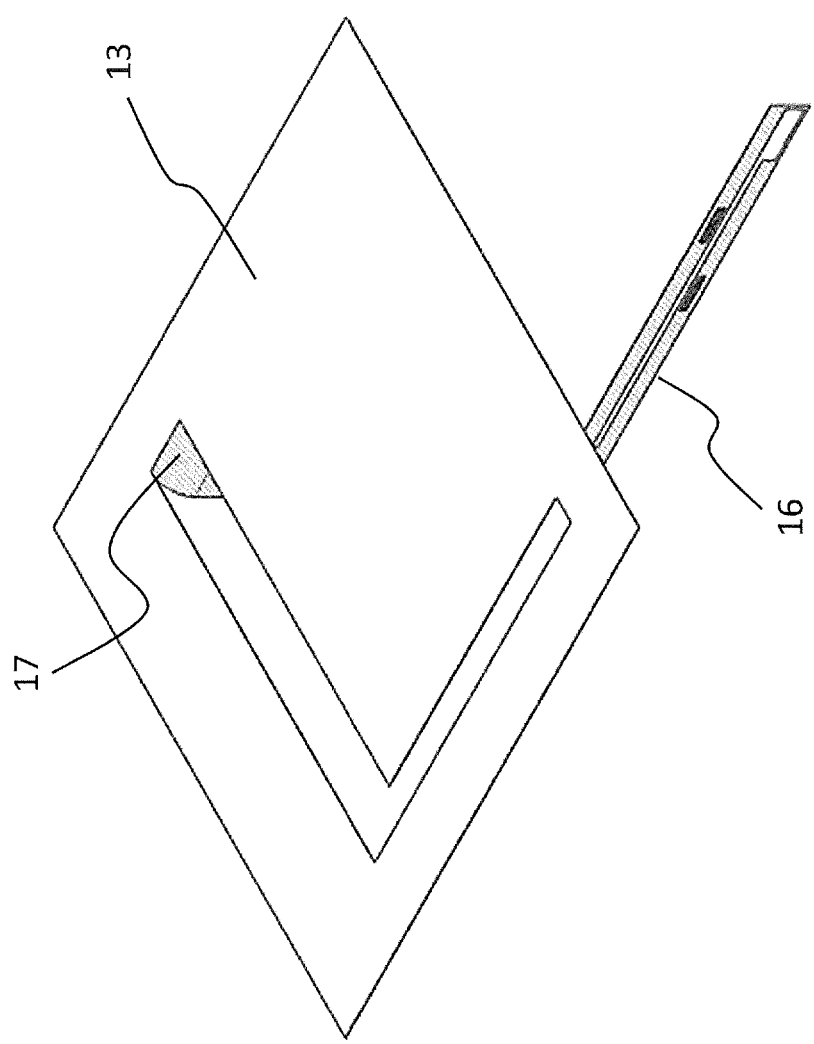
FIG. 11 is a partially detail oblique view of the sensor unit of FIG. 1.

In the present embodiment, as shown in FIGS. 8 and 11, the sensor 16 is substantially L-shaped, and the lateral side portion thereof is placed inside a well 8 and held in a horizontal state to sense the culture state in the well 8.

Also, a sensing electrode for sensing the culture state in the well 8 is formed on the lower lateral side portion the sensor 16. Increasing the electrode surface area of the sensing electrode increases the sensitivity of the sensor 16. The horizontal width of the lower lateral side portion the sensor 16 is wider than the horizontal width of the upper vertical side portion. The reason for this is to ensure sufficient surface area of the wiring 19 of the substrate 13. Increasing this surface area also increases the sensitivity of the sensor 16.

For this reason, since the sensor 16 is substantially L-shaped, the sensor 16 is formed by being cut out from the substrate 13 in a state in which the vertical side of the substantially L-shaped sensor 16 is inclined with respect to two opposing sides of the rectangular substrate 13.

The reason why the sensor 16 is cut out from the substrate 13 in a state of being inclined with respect to two opposite sides of the substrate 13 is that this ensures sufficient length of the vertical side portion (the vertically orientated portion in FIG. 12) of the sensor 16. This makes it possible to adjust the immersion of the sensing electrode formed on the lateral side portion (the laterally oriented portion in FIG. 12) of the sensor 16 with respect to the medium in the well 8.

The sensor 16 is not limited to being substantially L-shaped, and may be, for example, substantially I-shaped, substantially in an inverted T-shape, or any other shape so long as the shape is cut out to leave the bent portion 17 on the substrate 13. Also, in order to improve the sensitivity of the sensor 16, it is preferable to increase the horizontal width of the lateral side portion of the sensor 16.

As shown in FIGS. 12 to 15, a working electrode 21, a counter electrode 22, and a reference electrode 23 are provided on the lateral side portion of the sensor 16 as sensing electrodes.

Also, a silver layer (a silver layer and/or a silver chloride layer) 24 is provided on the surface of the reference electrode 23. A reagent layer 25 formed from an enzyme, a mediator, or the like is provided on the surface of the working electrode 21. These sensing electrode portions are covered with a protective film 29.

The sensor 16 electrochemically senses the concentration of a specific component of the medium by immersing the working electrode 21, the counter electrode 22, and the reference electrode 23 into the medium in the well 8.

For example, when sensing the concentration of the glucose component in a medium, the reagent layer 25 immobilized on the surface of the working electrode 21 contains an enzyme (such as GOx) and a redox mediator.

The principle by which glucose is thus sensed is that glucose that has permeated from the medium through the protective film 29 is oxidized by an enzymatic reaction with an enzyme (such as GOx) in the reagent layer 25 to become gluconolactone, and at the same time, the redox mediator in the reagent layer 25 is reduced into a reductant. The glucose concentration in the medium can be measured by measuring, as a current value, the electrons generated when this reductant goes back to being an oxidant.

The role of the protective film 29 is to allow the glucose in the medium to permeate into the sensing electrode portion of the sensor 16 while limiting permeation into the culture medium, and to prevent the outflow to the outside of the protective film of the enzyme and the mediator, which are the components of the reagent layer 25 immobilized on the working electrode 21.

The enzyme and the mediator are cross-linked and immobilized on the electrode. Therefore, since the reagent layer 25 is polymerized, the molecular weight increases. Consequently, the glucose can permeate, while the enzyme and mediator are prevented from flowing out of the protective film 29 (see WO2019/146788 for details).

The sensor 16 is formed on the substrate 13, and the manufacturing method thereof is as follows.

Figure 12:
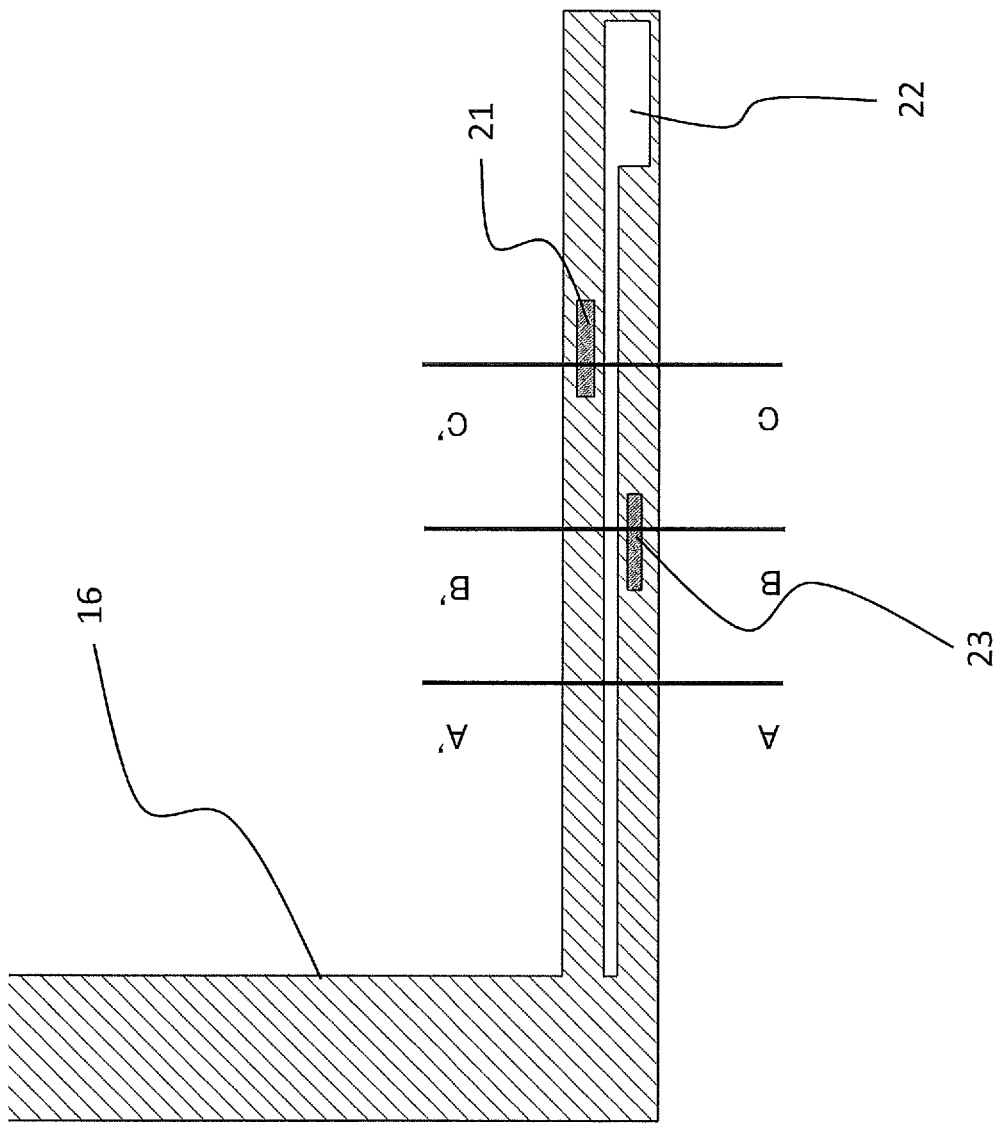
FIG. 12 is a partially detail plan view of the sensor unit of FIG. 1.
Figure 13:
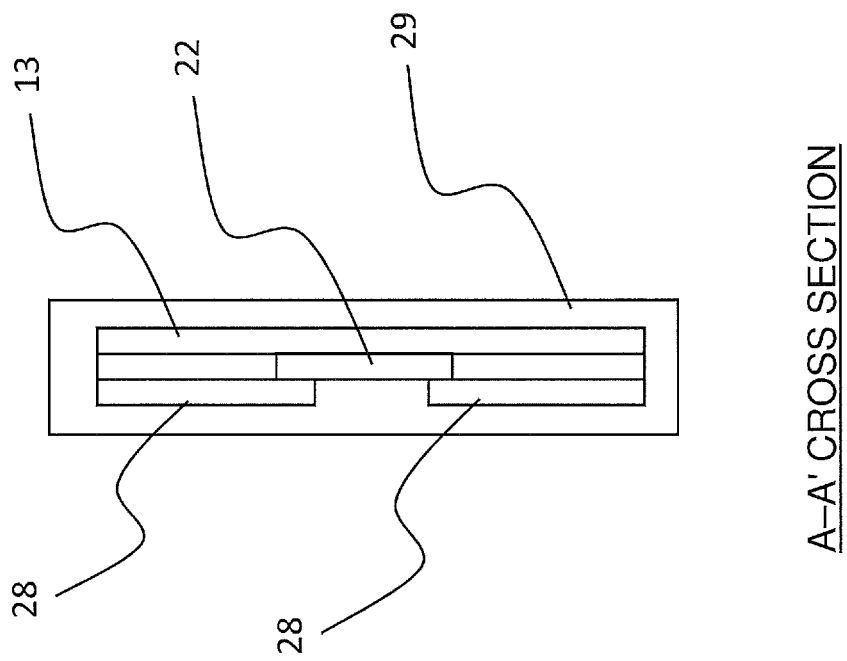
FIG. 13 is a cross-sectional view along the A-A line in FIG. 12.
Figure 14:
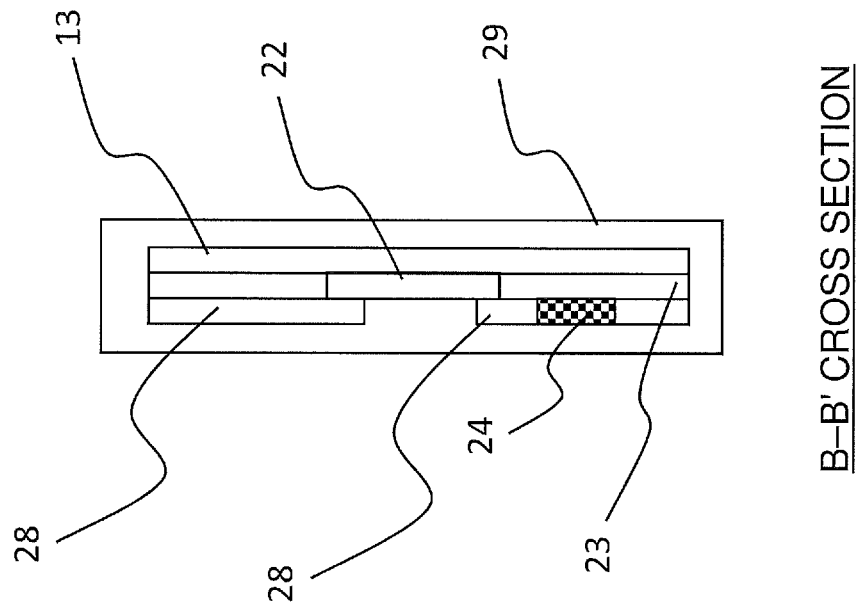
FIG. 14 is a cross-sectional view along the B-B line in FIG. 12.
Figure 15:
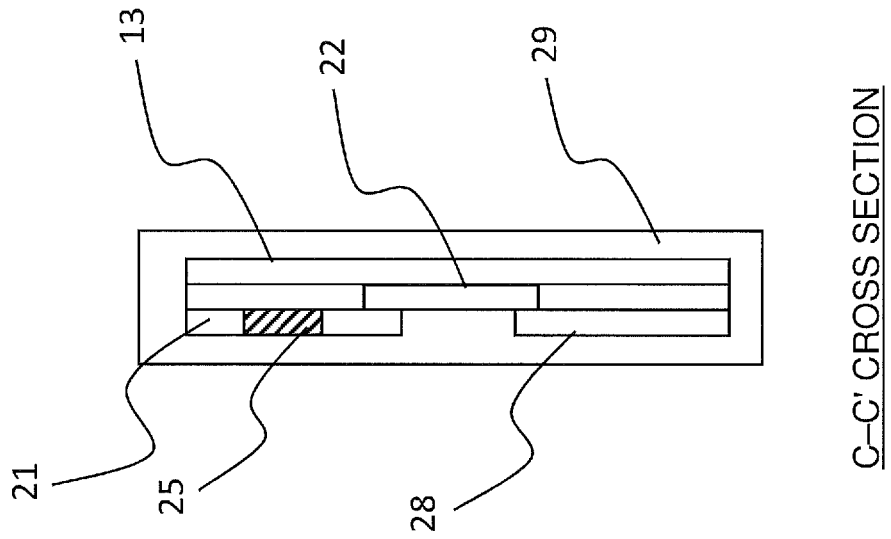
FIG. 15 is a cross-sectional view along the C-C line in FIG. 12.
Figure 16:
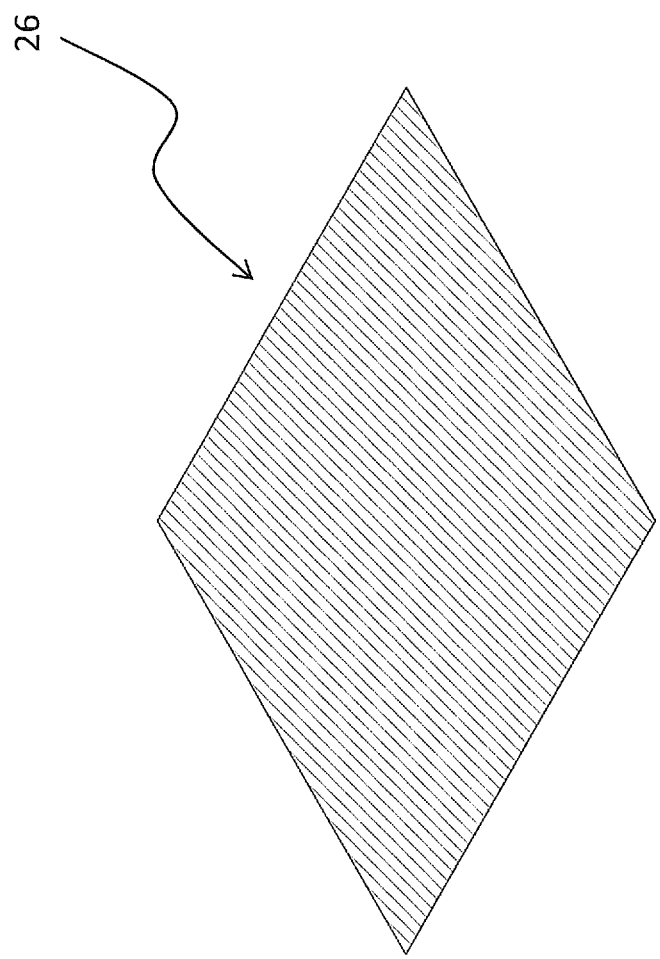
FIG. 16 is an oblique view of the method for manufacturing the sensor unit of FIG. 1.
Figure 17:
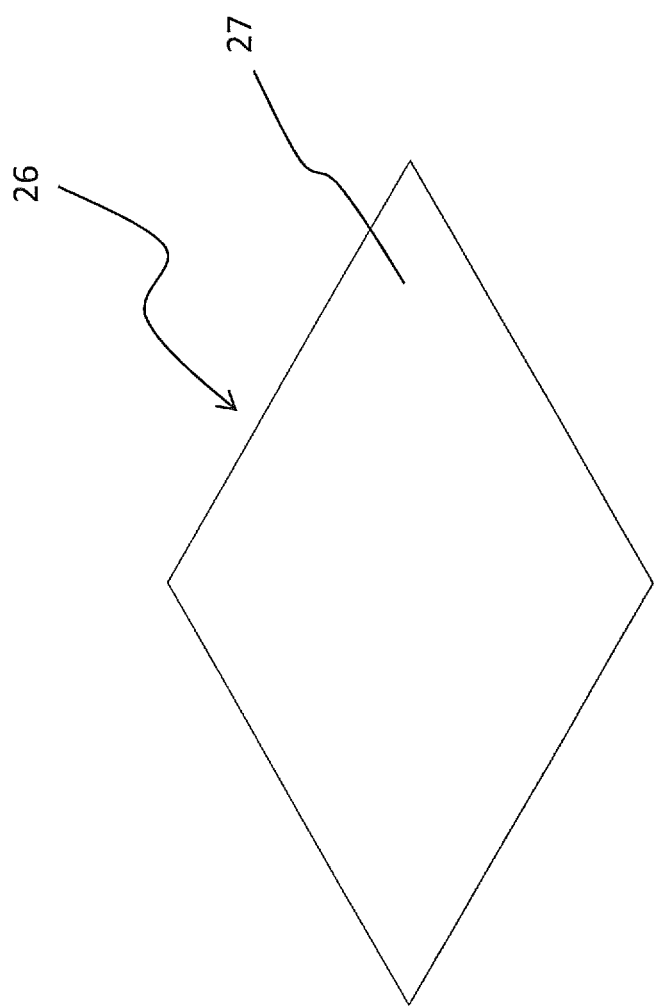
FIG. 17 is an oblique view of the method for manufacturing the sensor unit of FIG. 1.
Figure 18:
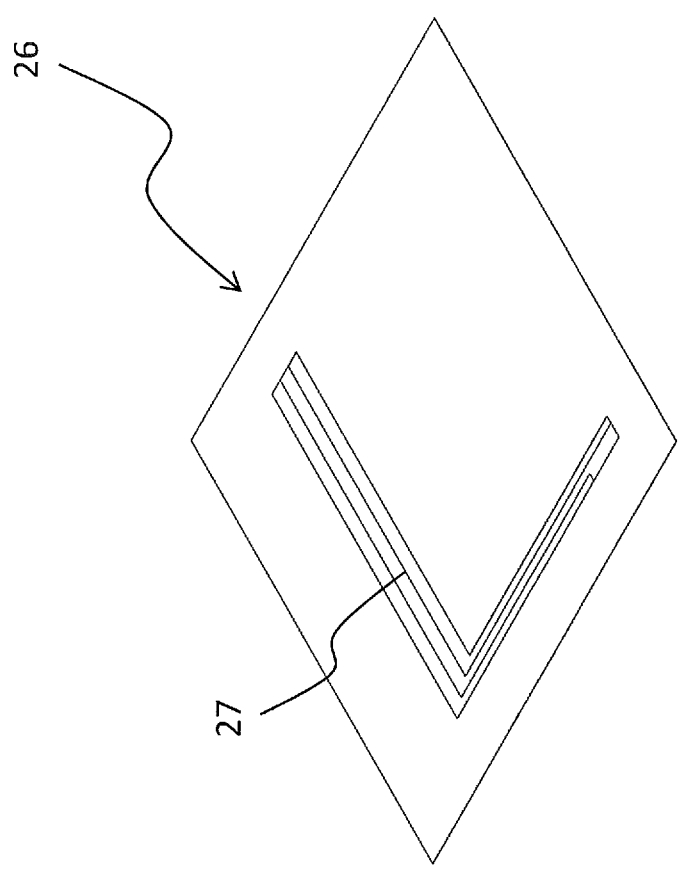
FIG. 18 is an oblique view of the method for manufacturing the sensor unit of FIG. 1.

That is, as shown in FIG. 16, a gold electrode layer 27 is formed by sputtering as shown in FIG. 17 on the upper surface of a PET (polyethylene terephthalate) film 26, which is a resin material. Next, as shown in FIG. 18, the electrode layer 27 is marked in an approximate L shape to match the sensor 16. That is, the electrode layer 27 is transpired with a laser, thereby forming a substantially L-shaped electrode layer 27. Further, as shown in FIG. 12, this substantially L-shaped electrode layer 27 is divided into an working electrode 21, a counter electrode 22, and a reference electrode 23. The three divided conduction paths are extended to the substrate 13 all the way to the bent portion 17, and each is connected to the wiring 19. Therefore, at the connecting portion 20, signals are taken off from the working electrode 21, the counter electrode 22, and the reference electrode 23.

Figure 19:
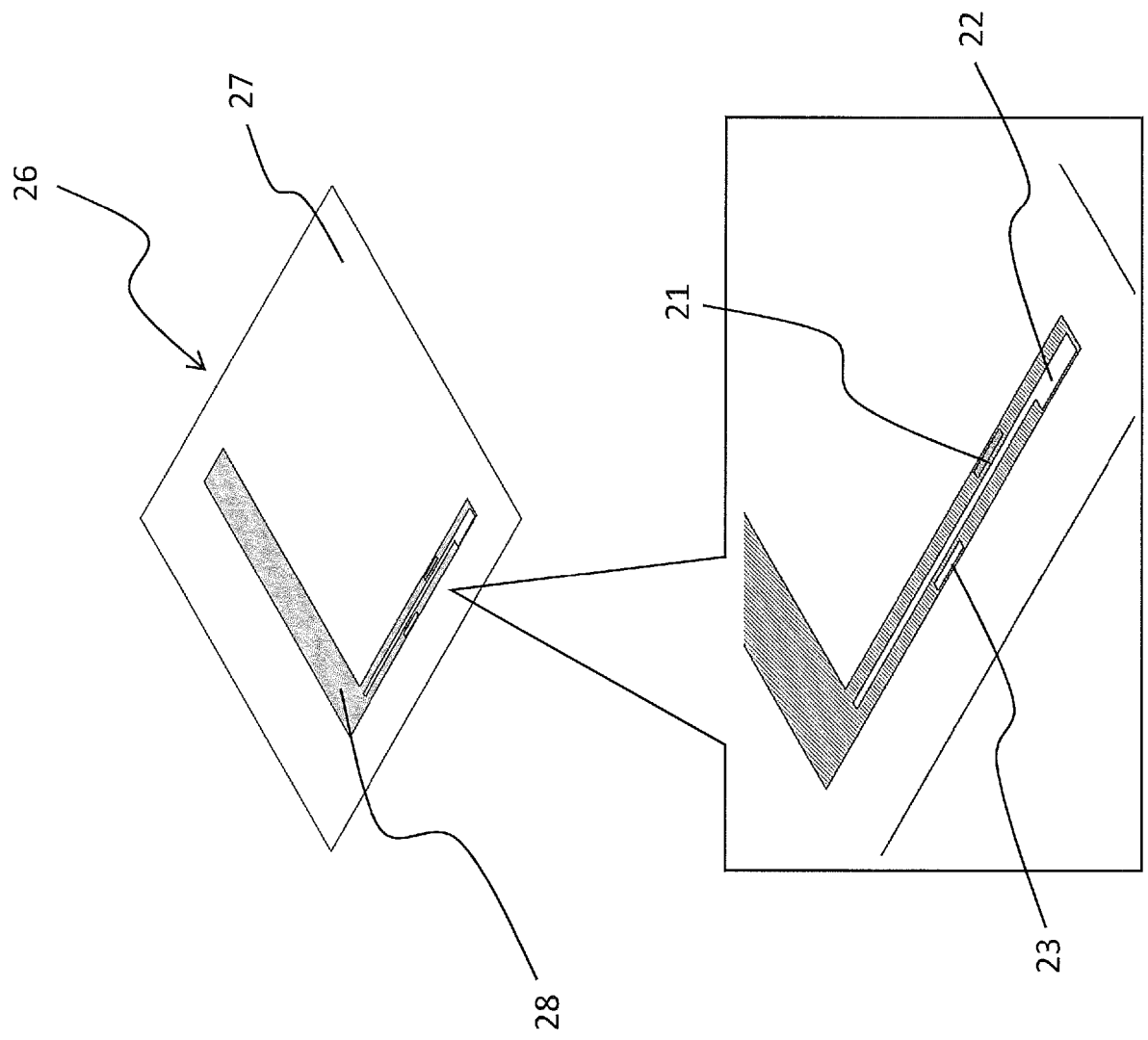
FIG. 19 is an oblique view of the method for manufacturing the sensor unit of FIG. 1.
Figure 20:
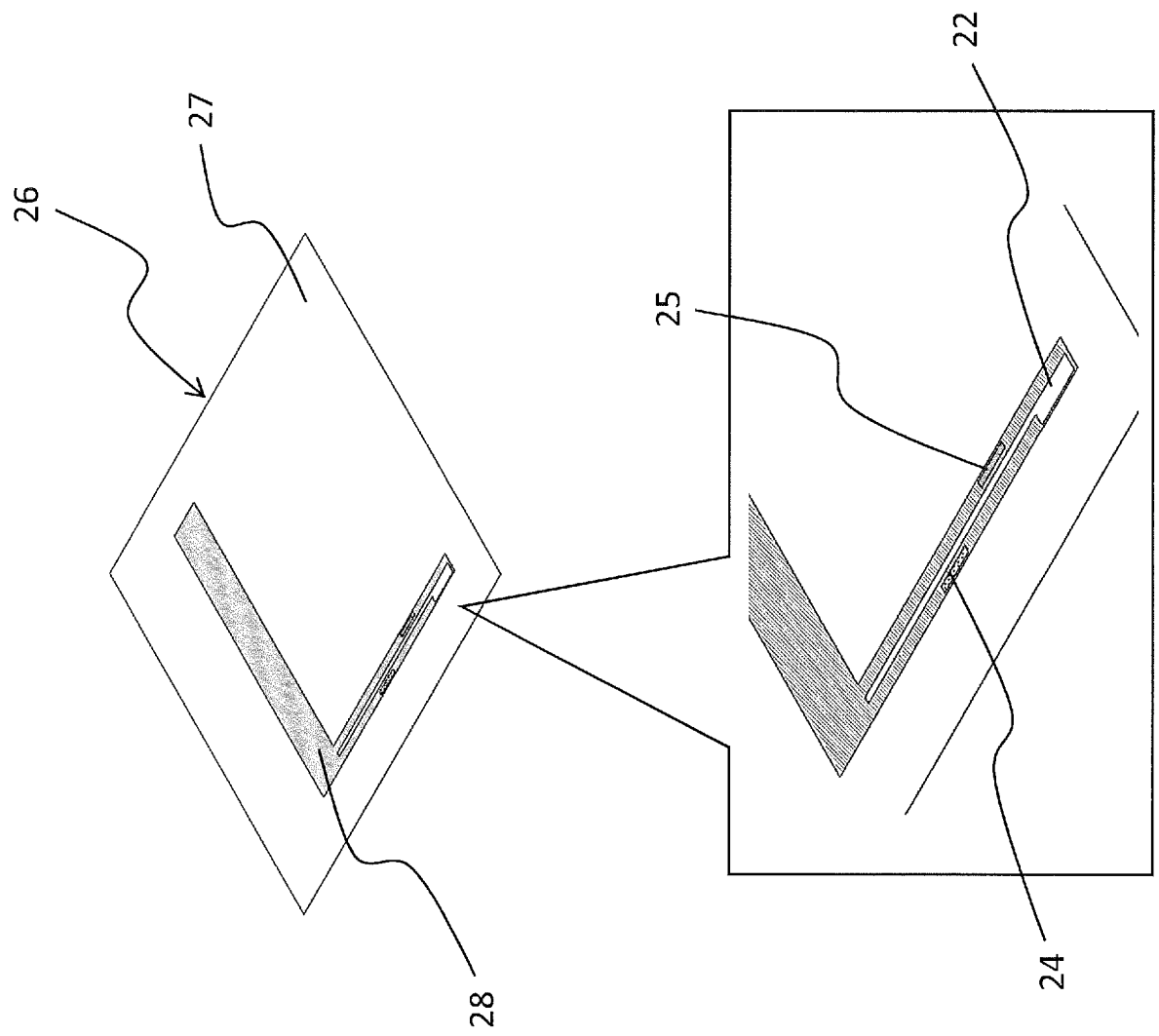
FIG. 20 is an oblique view of the method for manufacturing the sensor unit of FIG. 1.

After the substantially L-shaped electrode layer 27 is divided into the working electrode 21, the counter electrode 22, and the reference electrode 23, as shown in FIG. 19, the working electrode 21, the counter electrode 22, and the reference electrode 23 are masked, and a resist film 28 is provided in this state. After this, as shown in FIG. 20, a silver layer (a silver layer and/or a silver chloride layer) 24 is provided on the surface of the reference electrode 23, and a reagent layer 25 is provided on the surface of the working electrode 21.

Figure 21:
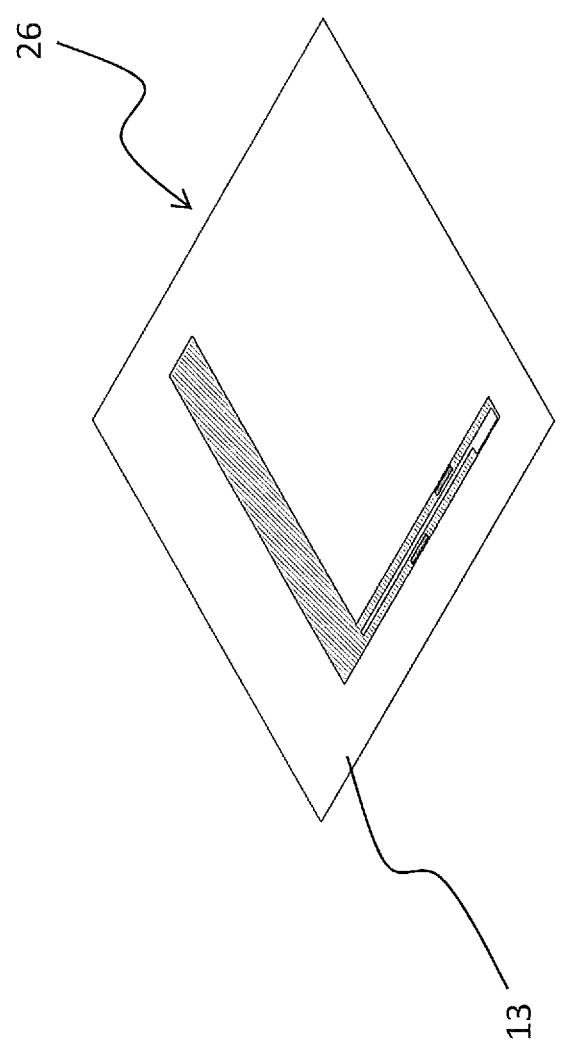
FIG. 21 is an oblique view of the method for manufacturing the sensor unit of FIG. 1.
Figure 22:
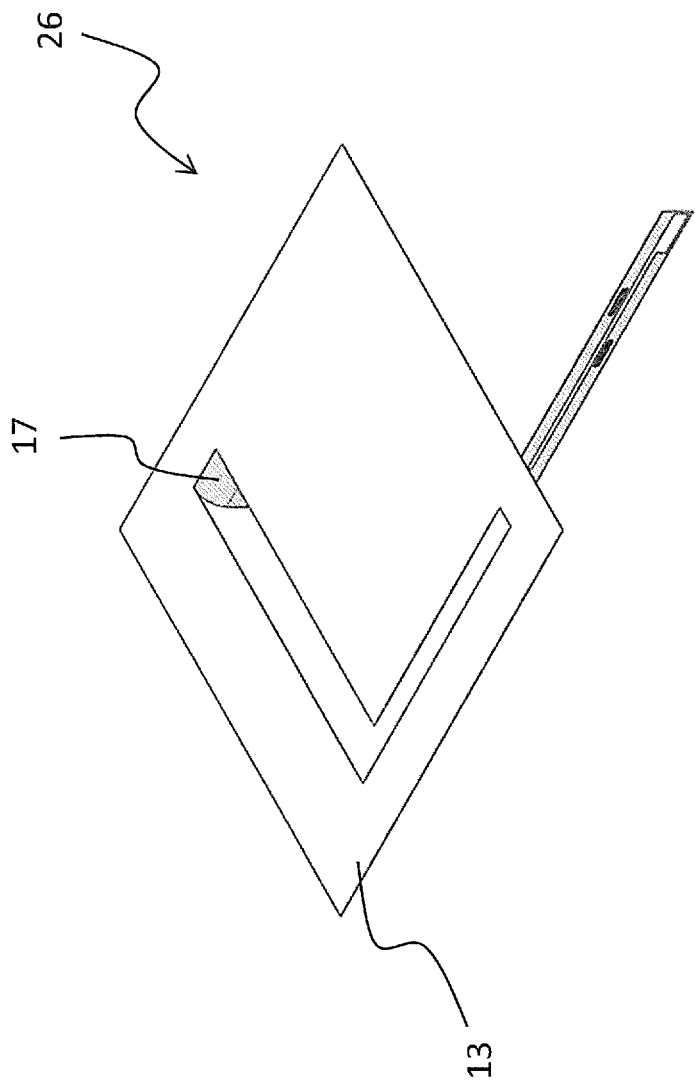
FIG. 22 is an oblique view of the method for manufacturing the sensor unit of FIG. 1.
Figure 23:
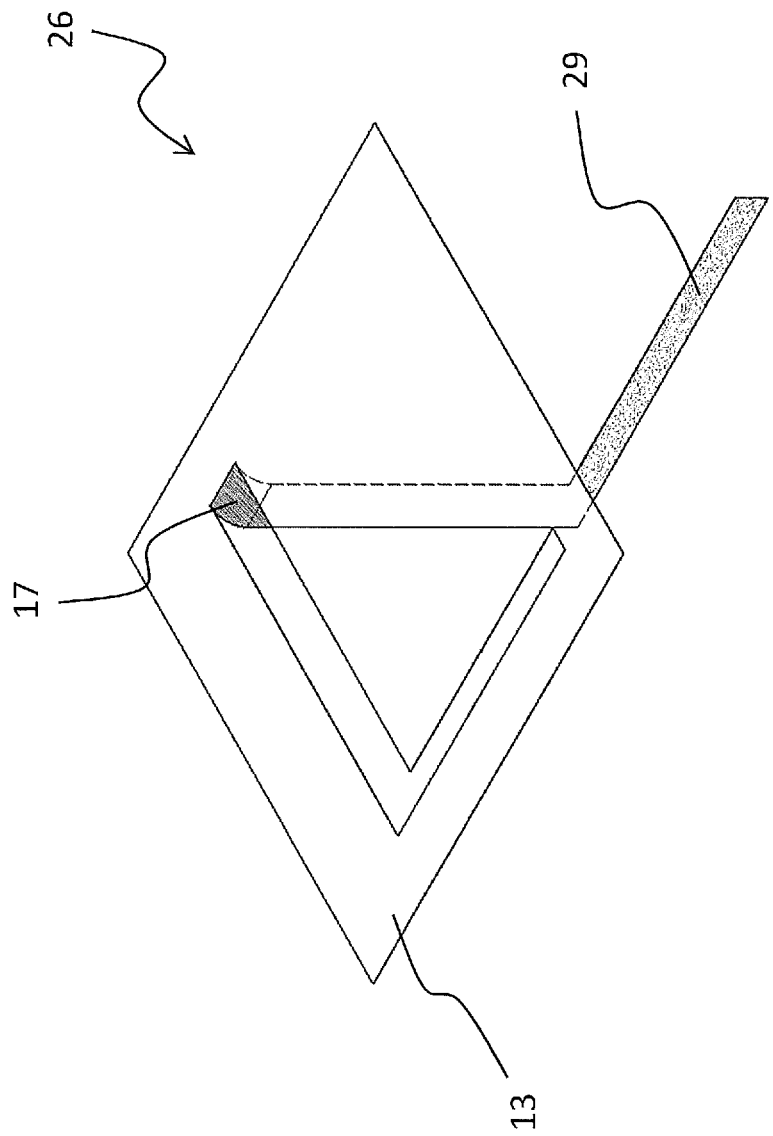
FIG. 23 is an oblique view of the method for manufacturing the sensor unit of FIG. 1.

Next, as shown in FIG. 21, the substrate 13 is irradiated with a laser in order to cut out the substantially L-shaped sensor 16 portion. In this state, in the substantially L-shaped sensor 16 is linked to the substrate 13 only at the bent portion 17. Consequently, as shown in FIG. 22, the sensor 16 is bent downward via the bent portion 17. Then, in this state, as shown in FIG. 23, the working electrode 21, the counter electrode 22, and the reference electrode 23 are covered with the protective film 29.

After this, as shown in FIG. 8, the substrate 13 is sandwiched between the top cover 15 and the bottom cover 14 from above and below. As shown in FIG. 7, the bottom cover 14 is provided with a through-hole 30. Consequently, the lateral side portion of the sensor 16 (the portion where the working electrode 21, the counter electrode 22, and the reference electrode 23 are located) goes through the through-hole 30 and is disposed below the bottom cover 14.

In this embodiment, as shown in FIG. 9, a support portion 31 that supports the lower side of the bent portion 17 of the sensor 16 is provided at the opening edge of the through-hole 30 in the bottom cover 14. A pressing portion 32 that pushes the upper side of the bent portion 17 of the sensor 16 downward is provided at the portion of the top cover 15 that is opposite the support portion 31.

These support portions 31 have an upper surface curved shape. Also, the pressing portion 32 has a lower surface curved shape.

As a result, as shown in FIGS. 8 and 9, when the substrate 13 is sandwiched between the top cover 15 and the bottom cover 14 from above and below, the bent portion 17 of the sensor 16 is sandwiched by the support portion 31 and the pressing portion 32 from above and below. Consequently, the lateral side portion of the sensor 16 (the portion where the working electrode 21, the counter electrode 22, and the reference electrode 23 are located) can be maintained in a stable state below and disposed substantially along the horizontal direction.

Once in this substantially horizontal state, the lateral side portion of the sensor 16 (the portion where the working electrode 21, the counter electrode 22, and the reference electrode 23 are located) can be held in a stable position in each well 8 of the culture vessel 7, and the culture status inside each well 8 can be appropriately sensed.

Also, since the curvature of the arc portion of the bent portion 17 of the sensor 16 is defined by the bottom cover 14 and the top cover 15, and excessive stress will not be exerted on the bent portion 17, so is possible to prevent disconnection due to cracking.

As to how the bent portion 17 is bent, either the top cover 15 or the bottom cover 14 may be bent in a state of having been attached to the substrate 13. Also, heat may be applied to the bent portion 17 during the bending. In that case, the top cover 15 and the bottom cover 14 are unnecessary.

As described above, in this embodiment, the sensor 16 is formed so as to be cut out from the substrate 13 in a state in which the bent portion 17 remains behind, and is bent downward with respect to the substrate 13. This eliminates the need for a component for fixing the sensor 16 to the substrate 13, and allows the sensor unit 9 to be more compact.

Also, as the configuration of the sensor 16, since the sensor 16 and the wiring portion on the substrate 13 can be formed integrally, there is no need for a connector between the sensor 16 and the wiring 19. This allows the sensor unit 9 to be more compact.

Also, the wiring 19 of the substrate 13 is collected as a wiring pattern on the substrate 13, and is gathered into the connection portions 20a and 20b. Since the connection portions 20a and 20b are connected to the connector of the control unit 12, there is no need to connect the sensor unit 10 and the control unit 12 with wiring such as a lead wire. This allows the cell culture analysis device 3 itself to be more compact.

Figure 24:
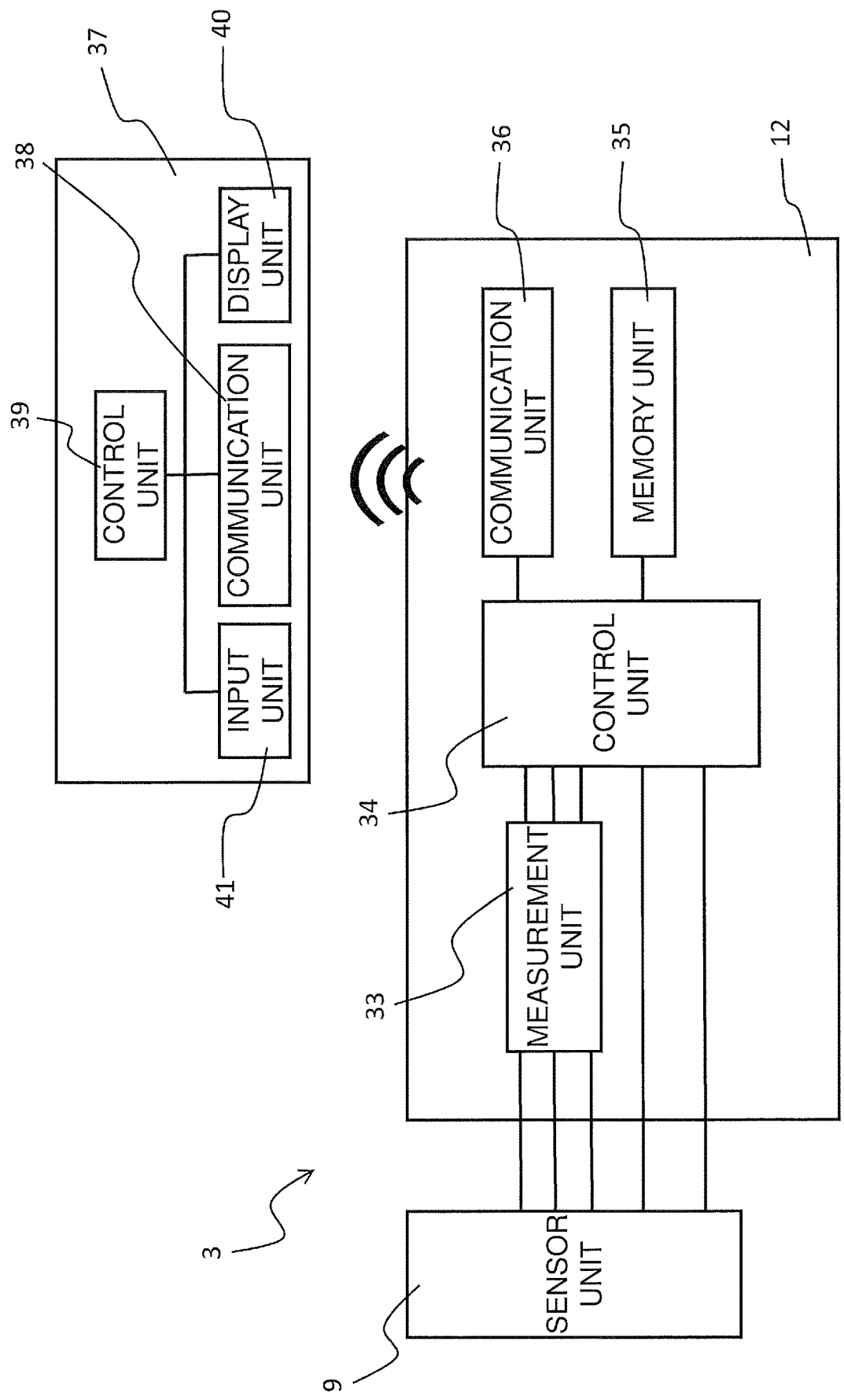
FIG. 24 is a control block diagram of the cell culture analysis device of FIG. 1.

FIG. 24 shows a control block of the cell culture analysis device 3. Information about the inside of the wells 8 sensed as above is transmitted to a control unit 34 via a measurement unit 33 provided in the control unit 12, stored in the storage unit 35, and transmitted to a communication unit 38 of an external device 37 (personal computer) via a communication unit 36. The external device 37 can display the sensing data on a display unit 40 via a control unit 39. 41 in the drawings is an input unit of the external device 37.

As described above, in this embodiment, even when many wells 8 are used as shown in FIGS. 5 and 8, the culture status can be sensed at once by the extremely compact sensor unit 9. That is, a major feature of the cell culture analysis device 3 in this embodiment is that the sensor unit 9 is smaller in size.

In this embodiment, the sensor 16 is cut out from the substrate 13 and bent downward while the bent portion 17 is left on the substrate 13. This eliminates the need for a component for fixing the sensor 16 to the substrate 13, and the sensor unit 9 can be more compact.

Embodiment 2

FIGS. 25 to 28 show the configuration of the sensor unit 9 in another embodiment of the present invention. That is, in this embodiment, the sensor 16 is substantially I-shaped, and the upper portion of the vertical side of the sensor 16 serve as the bent portion 17, which is different from the configuration of the sensor unit 9 in Embodiment 1 above.

Also, the difference between FIGS. 25 and 26 and FIGS. 27 and 28 is that the sensor 16 is wider in the former than in the latter. Also, in the configurations shown in FIGS. 25 and 26, the vertical side of the sensor 16 is cut out from the substrate 13 in a state of being inclined with respect to two opposing sides of the rectangular substrate 13.

Figure 25:
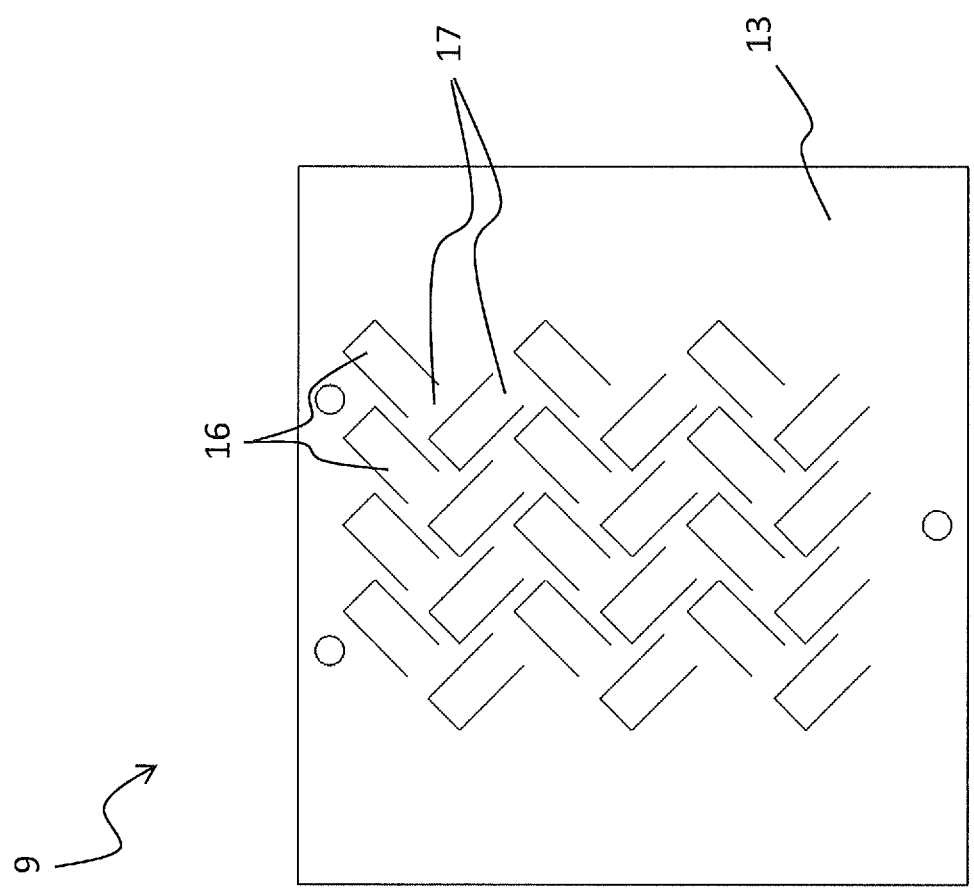
FIG. 25 is a plan view of the sensor unit according to another embodiment of the present invention.
Figure 26:
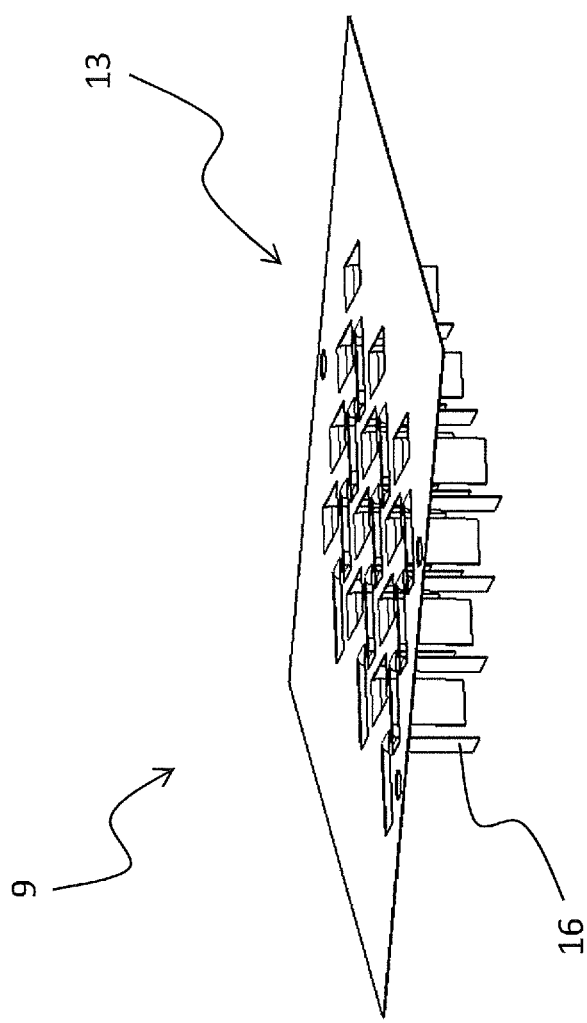
FIG. 26 is an oblique view of the sensor unit of FIG. 25.

Also, as shown in FIG. 25, a plurality of rows of sensor groups are provided in which a plurality of sensors 16 are disposed, and the sensors 16 in adjacent rows are disposed so as to be inclined in the opposite directions in the left-right direction in the drawing.

Figure 27:
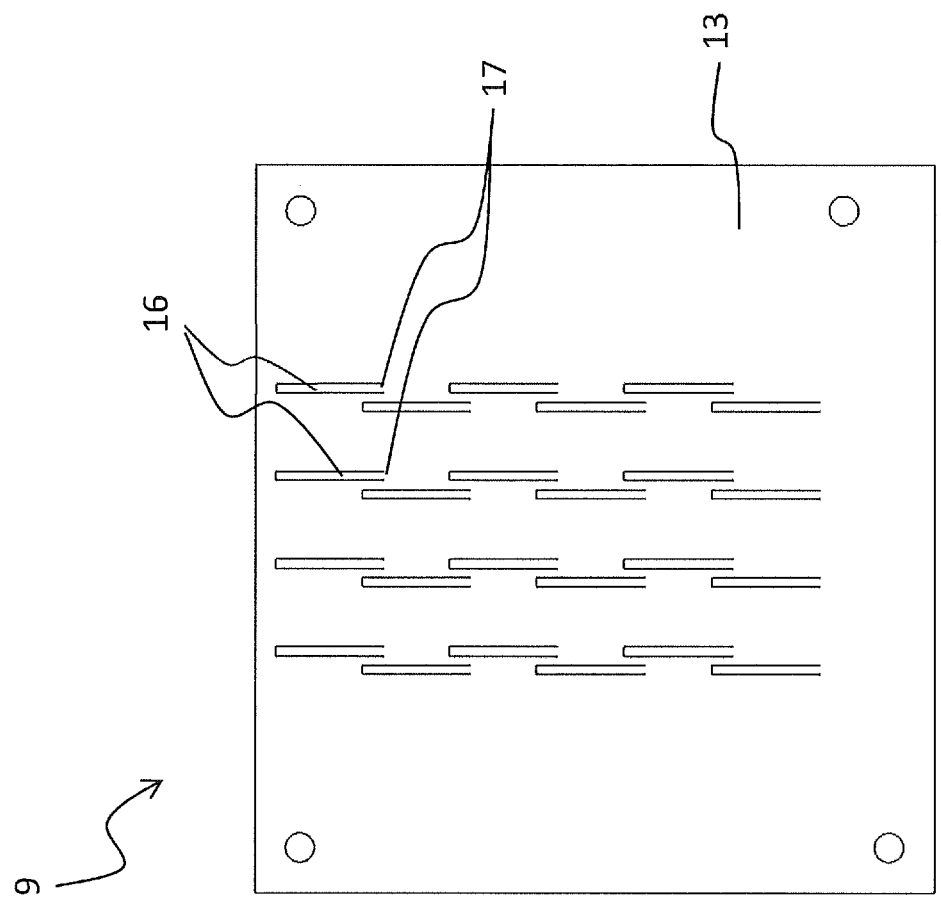
FIG. 27 is a plan view of the sensor unit according to yet another embodiment of the present invention.
Figure 28:
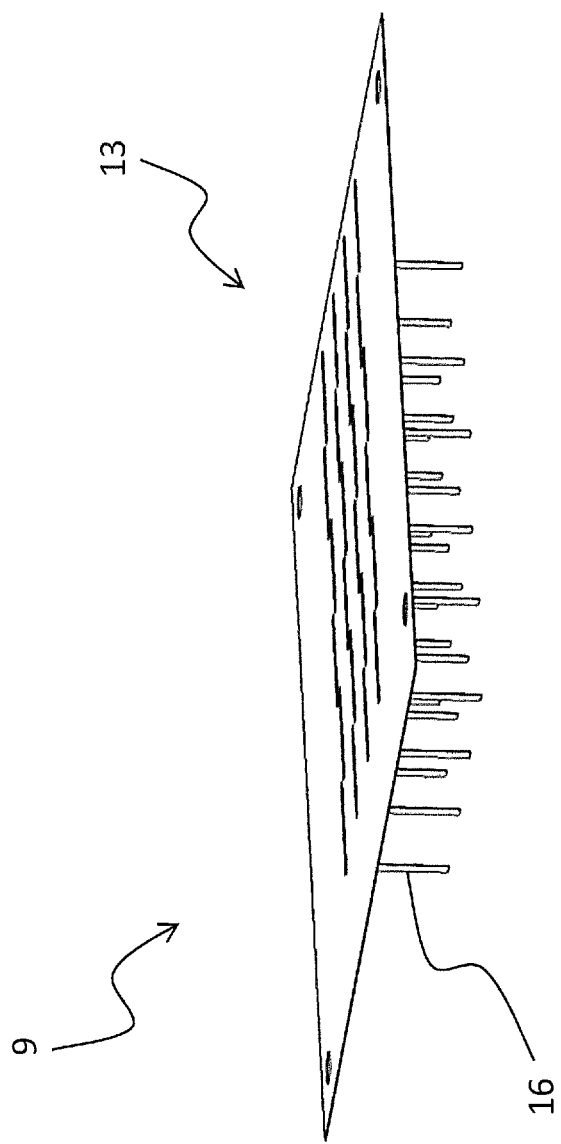
FIG. 28 is an oblique view of the sensor unit of FIG. 27.

By contrast, in the sensor unit 9 shown in FIGS. 27 and 28, a plurality of sensors 16 are arranged in the vertical direction on the substrate 13, and a plurality of rows of sensor groups are provided such that some are adjacent to each other in the left-right direction.

Also, in each row, the adjacent sensors 16 are disposed alternately on the left and right with respect to the center line of the row.

INDUSTRIAL APPLICABILITY

With the sensor unit of the present invention, the sensor is formed by being cut out from the substrate, leaving on the substrate a bent portion where the sensor is bent downward, so there is no need for a component for fixing the sensor to the substrate, the effect of which is that the size can be reduced, so this sensor unit can be used in the field of cell culture devices that need to be compact in size.

REFERENCE SIGNS LIST 1 cell culture device
2 culture room
3 cell culture analysis device
4 door
5 main body case
6 culture vessel installation part
7 culture vessel
8 well
9 sensor unit
10 leg (support portion)
11 positioning hole
12 control unit
13 substrate
14 bottom cover
15 top cover
16 sensor
17 bent part
18 L-shaped part
18a vertical side cutout portion
18b lateral side cutout portion
19 wiring
20a, 20b connection portion
21 working electrode
22 counter electrode
23 reference electrode
24 silver layer
25 reagent layer
26 PET (polyethylene terephthalate) film
27 electrode layer
28 resist film
29 protective film
30 through-hole
31 support portion
32 pressing portion
33 measurement unit
34 control unit
35 memory unit
36 communication unit
37 external device
38 communication unit
39 control unit
40 display unit
41 input unit

The invention claimed is:

1. A sensor unit, comprising
a substrate having a sensor of which a sensing electrode is provided at a tip portion, wiring that is connected to the sensor, connection portions that are connected to the sensor via the wiring, and a bent portion where the sensor is bent downward,
the sensor is formed by being cut out from the substrate, leaving the bent portion on the substrate, and wherein the sensor is immersed in a liquid sample.

2. The sensor unit according to claim 1,
wherein a plurality of the sensors are provided on the substrate.

3. The sensor unit according to claim 1,
further comprising a bottom cover that is provided below the substrate, and a top cover that is provided above the substrate,
wherein the substrate is configured to be sandwiched between the bottom cover and the top cover from above and below.

4. The sensor unit according to claim 3,
wherein the bottom cover is provided with a through-hole down through which the sensor is passed.

5. The sensor unit according to claim 4,
wherein a support portion for supporting a lower side of the bent portion of the sensor is provided to an opening edge of the through-hole of the bottom cover, and
a pressing portion for pushing an upper side of the bent portion of the sensor downward is provided to a portion of the top cover that is opposite the support portion.

6. The sensor unit according to claim 5,
wherein the support portion has an upper surface curved shape, and the pressing portion has a lower surface curved shape.

7. The sensor unit according to claim 1,
wherein the sensor is substantially L-shaped, and an upper portion of a vertical side of the sensor is used as the bent portion.

8. The sensor unit according to claim 7,
wherein the substrate is formed in a rectangular shape, and the vertical side of the sensor is cut out from the substrate in a state of being inclined with respect to two opposing sides of the substrate.

9. The sensor unit according to claim 7,
wherein a first sensor and a second sensor that is disposed adjacent to the first sensor are formed on the substrate by being cut out, and the wiring connected to the bent portion connecting the first sensor and the substrate is taken out to an outer peripheral portion of the substrate in between a vertical side cutout portion of the first sensor and a lateral side cutout portion of the second sensor.

10. The sensor unit according to claim 1,
wherein the sensor is substantially I-shaped, and an upper portion of a vertical side of the sensor is used as the bent portion.

11. The sensor unit according to claim 10,
wherein the substrate has a rectangular shape, and the sensor is formed by being cut out from the substrate in a state in which the vertical sides of the sensor are inclined with respect to two opposing sides of the substrate.

12. The sensor unit according to claim 11,
wherein the substrate is provided with a plurality of rows of sensor groups in which a plurality of the sensors are arranged, and
the sensors in adjacent rows are disposed in a state of being inclined in an opposite direction.

13. The sensor unit according to claim 12,
wherein the substrate is provided with a plurality of rows of sensor groups in which a plurality of the sensors are arranged, and in each row, the adjacent sensors are disposed alternately on left and right with respect to a center line of the row.

14. A cell culture analysis device, comprising:
the sensor unit according to claim 1; and
a culture vessel installation part on which the sensor unit is placed.

15. The cell culture analysis device according to claim 14,
wherein the sensor unit is provided with legs for ensuring housing spaces for culture vessels on the culture vessel installation part, and the sensor unit is disposed on the culture vessel installation part on these legs.

16. The cell culture analysis device according to claim 14,
wherein a control unit configured to control the sensor unit is disposed on the sensor unit.

* * * * *